US00PP32319P2

(12) United States Plant Patent
Jones

(10) Patent No.: US PP32,319 P2
(45) Date of Patent: Oct. 13, 2020

(54) ***DIANTHUS* PLANT NAMED 'DCARE11-0'**

(50) Latin Name: *Dianthus hybrida*
Varietal Denomination: DCARE11-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/501,877

(22) Filed: Jun. 19, 2019

(51) Int. Cl.
*A01H 5/02* (2018.01)
*A01H 6/30* (2018.01)

(52) U.S. Cl.
USPC ..... Plt./278

(58) Field of Classification Search
USPC ..... Plt./272, 273, 278
See application file for complete search history.

*Primary Examiner* — Susan McCormick Ewoldt
(74) *Attorney, Agent, or Firm* — Cassandra Bright

(57) ABSTRACT

A new and distinct *Dianthus* cultivar named 'DCARE11-0' is disclosed, characterized by continuous flowering on floriferous plants hardy to USDA Zone 3. Flowers are semi-double and uniquely true red. The new variety is a *Dianthus*, typically produced as a garden or container plant.

2 Drawing Sheets

Latin name of the genus and species: *Dianthus hybrida.*
Variety denomination: 'DCARE11-0'.

BACKGROUND OF THE INVENTION

The new cultivar is a product of chance discovery. The new variety originated as a spontaneous whole plant mutation discovered among a commercial planting of the unpatented parent *Dianthus* 'Magical Cherry'. 'DCARE11-0' was discovered by the inventor, Steve Jones, at a commercial greenhouse in Santa Paula, Calif. during April of 2016.

Asexual reproduction of the new cultivar 'DCARE11-0' was first performed in Santa Paula, Calif. at a commercial greenhouse by terminal vegetative cuttings in May of 2016. 'DCARE11-0' has since produced several generations and has shown that the unique features of this cultivar are stable and reproduced true to type.

SUMMARY OF THE INVENTION

The cultivar 'DCARE11-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCARE11-0'. These characteristics in combination distinguish 'DCARE11-0' as a new and distinct *Dianthus* cultivar:

1. Floriferous plants.
2. Suitability for both garden and container uses.
3. Distinctive true red flower.
4. Continuous flowering from Spring through Fall. Repeat flowering enhanced by removal of spent flowers.
5. Hardy to USDA zone 3
6. Semi-double flower with an average of 18 to 25 petals.

Plants of the new cultivar 'DCAMC10-0' are comparable to parent 'Magical Cherry' in most horticultural characteristics. However, the new variety 'DCARE11-0' differs in the following:

1. The new variety produces flowers colored Red (46B) with a white base. The seed parent produces flowers which are Red-Purple with a white base.
2. Plants of the new variety are more floriferous than plants of the seed parent.

COMMERCIAL COMPARISON

Plants of the new cultivar 'DCARE11-0' are comparable to the commercial *Dianthus* variety 'DCACR08-0', U.S. Plant Pat. No. 30,026. The two *Dianthus* varieties are similar in most horticultural characteristics; however, the new variety 'DCARE11-0' produces a flower with a true red flower color, this comparator produces a medium pink to purple colored flower.

Plants of the new cultivar 'DCARE11-0' can also be compared to the commercial *Dianthus* variety 'DDTHP02-0', U.S. Plant Pat. No. 28,102. These varieties are similar in most horticultural characteristics; however 'DCARE11-0' produces a true red flower, compared to the lighter purple flower of this comparator.

BRIEF DESCRIPTION OF THE PHOTOGRAPHS

Figure 1:
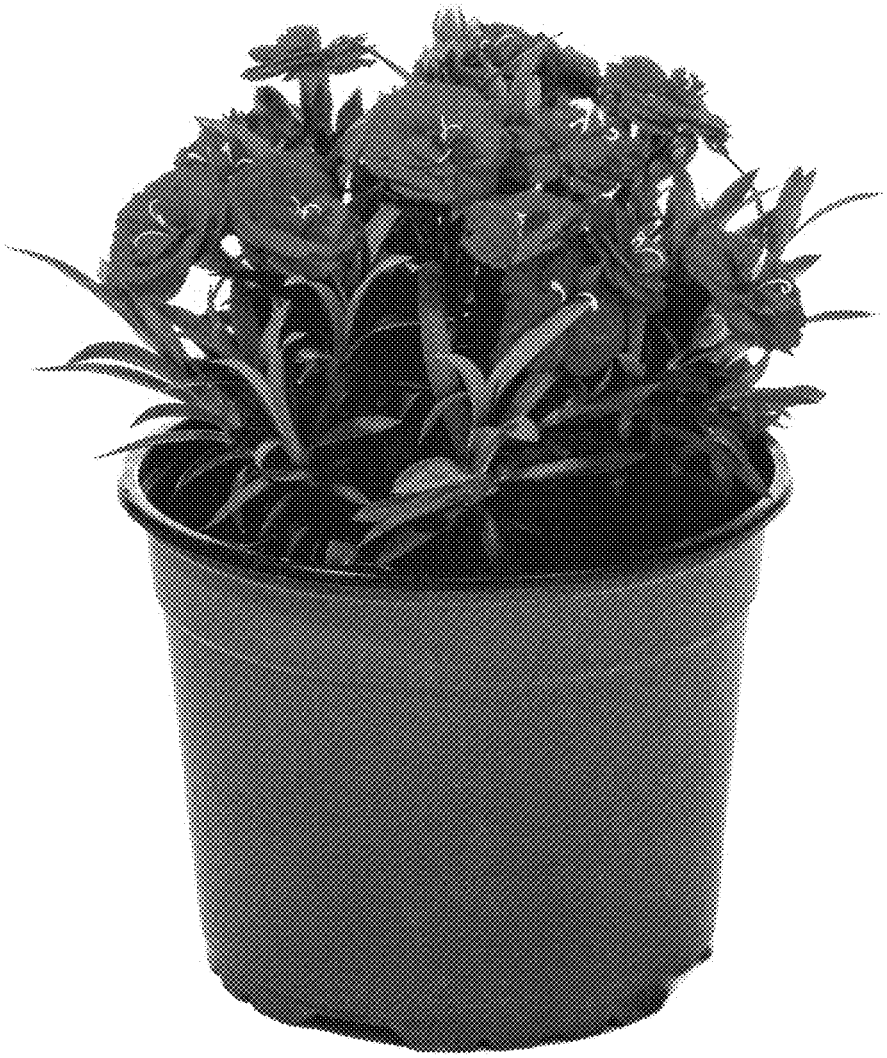

The accompanying photograph in FIG. 1 illustrates in full color a typical plant of 'DCARE11-0' grown outdoors in Santa Paula, Calif. This plant is approximately 20 weeks old, shown in a 1 gallon pot.

Figure 2:
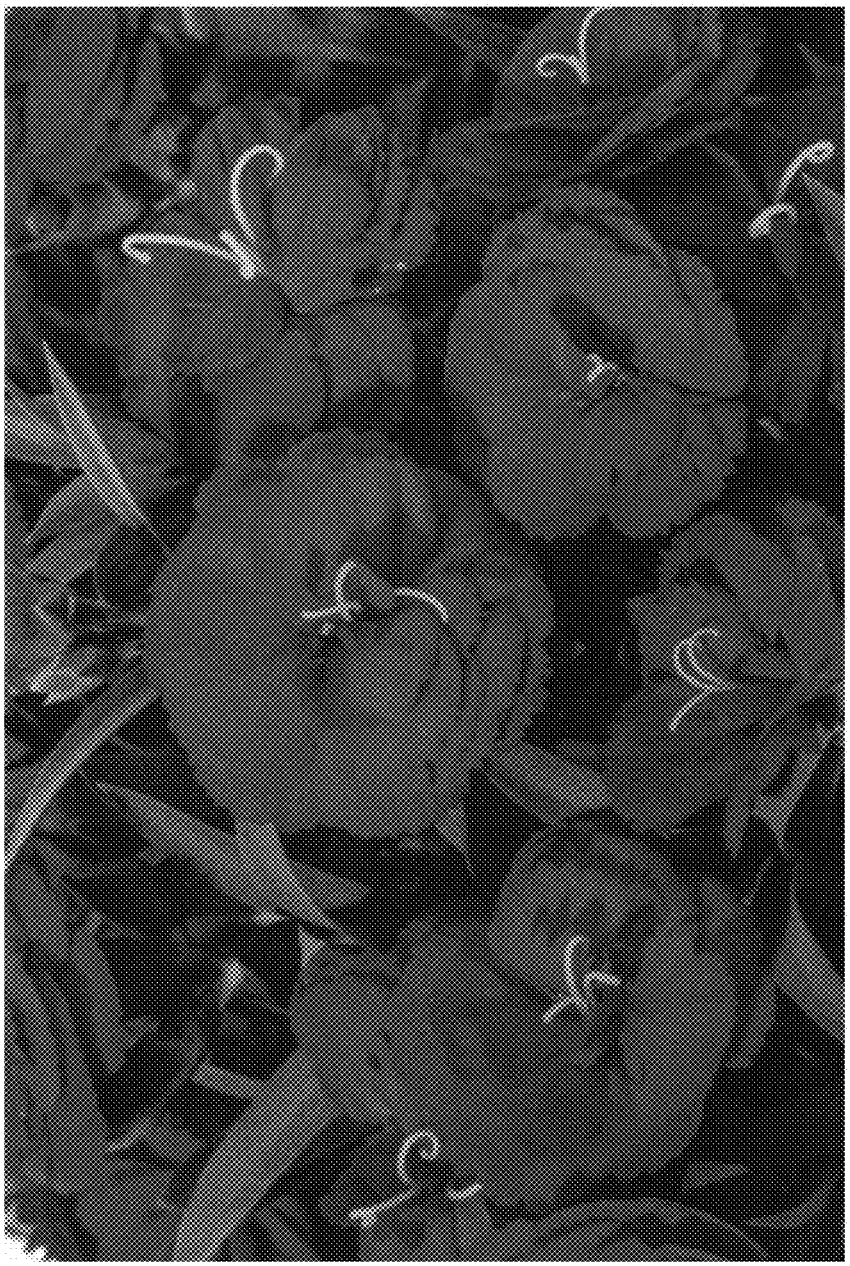

FIG. 2 illustrates a close up view of the flowers. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'DCARE11-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus hybrida* 'DCARE11-0'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near Orange- White 159C.

PLANT

Age of plant described: Approximately 20 weeks from rooted cutting.

Pot size: 6 inches.

Plant type: Compact upright perennial.

Plant habit: Upright growing stems emerge basally.

Plant spread: Approximately 25 cm.

Height: Approximately 16 cm to top of flowering plane. Approximately 14 cm to top of foliar plane.

Length plant stem: Average range 10 to 12.5 cm.

Diameter of plant stem: Approximately 3 mm.

Quantity stems: Approximately 30.

Stem:

*Color*.—Near RHS Yellow-Green 145C.

*Texture*.—Smooth.

Internode length: Average 3.2 cm.

FOLIAGE

Leaf:

*Arrangement*.—Opposite (in pairs).

*Quantity*.—Approximately 6-10 fully expanded per stem. Average range of 2-4 immature leaves per stem.

*Average length*.—Average range 4.2-5 cm.

*Average width*.—Approximately 0.5 cm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Color*.—Young foliage upper side: Near RHS Green 139A. Young foliage under side: Near RHS Green 139A. Mature foliage upper side: Between RHS Green 139A. Mature foliage under side: Near RHS Green 137A.

*Venation*.—Type: Linear with a prominent mid vein. Venation color upper side: Indistinguishable from foliage. Venation color under side: Indistinguishable from foliage.

FLOWER

Natural flowering season: Perpetual flowering.

Inflorescence type and habit: Umbel of 2 to 5 flowers.

Flower longevity on plant: 2-3 weeks.

Quantity of flowers: Approximately 40 flowers on a 20 week old plant.

Flowers persistent or self-cleaning: Persistent.

Fragrance: Moderately strong sweet scent.

Inflorescence size:

Diameter.—Approximately 5.0 cm.

Height.—Approximately 4.0 cm.

Individual flower size:

*Diameter*.—Approximately 3.0 cm.

*Length*.—Approximately 3.0 cm.

Petals:

*Petal arrangement*.—Whorled, multiple whorl.

*Shape*.—Spatulate, with an elongated narrow base and orbicular distal section.

*Base*.—Attenuate.

*Margin*.—Serrated.

*Apex*.—Sharply serrated or notched.

*Length*.—3.0 cm.

*Width*.—1.5 cm.

*Petal quantity*.—Average range 18 to 25.

*Texture*.—Smooth all surfaces.

*Aspect*.—Flat to slightly undulating.

Color:

*When opening*.—Upper surface: Near RHS Red 46A. Base near White N155A. Lower surface: Near RHS Red 46B. Base near White N155A.

*Fully opened*.—Upper surface: Near RHS Red 46B. Base near White N155A. Lower surface: Near RHS Red 46B. Base near White N155A.

*Fading*.—Upper surface: Near Red 46C. Base near White N155A. Lower surface: Near Red 46C. Base near White N155A.

Tube:

General description: Tube consists of the elongated, unfused base of the petals. Tube shape caused by a fused calyx.

*Length*.—1.7 cm.

*Width*.—0.8 cm.

*Texture*.—Smooth.

Color:

*Fully opened*.—Inner surface: Near RHS Green 139D. Outer surface: Near RHS Green 139C.

Bud:

*Shape*.—Elongated cylinder.

*Length*.—Average 2.5 cm.

*Diameter*.—Average 0.8 cm.

*Color*.—Near RHS Green 139C.

Sepals:

*Quantity*.—5.

*Arrangement*.—Fused tube.

*Shape*.—Cylindric.

*Length*.—1.5 cm.

*Width*.—0.4 cm.

*Margin*.—Entire.

*Apex*.—Acute.

*Texture*.—Smooth upper and lower surfaces.

*Color*.—Near RHS Green 139B upper and lower surfaces.

Bracteoles:

*Shape*.—Strap shaped.

*Quantity per flower*.—2.

*Length*.—Approximately 1.0 cm.

*Width*.—Approximately 2.0 mm.

*Margin*.—Entire.

*Texture*.—Smooth.

*Color*.—Near RHS Green 139A upper and lower surfaces.

Peduncle:

*Length*.—Average 3.0 cm.

*Diameter*.—1.0 mm.

*Color*.—Near RHS Green 139A.

*Orientation*.—Upright.

*Strength*.—Flexible.

*Texture*.—Smooth.

Pedicel:

*Length*.—Average 0.8 cm.

*Diameter*.—1 mm.

*Color*.—Near RHS Greyed-Green 139B.

*Orientation*.—Upright.

*Strength*.—Flexible, elastic.

REPRODUCTIVE ORGANS

Stamens:

*Number*.—Most commonly 6.

*Filament length*.—Approximately 1.2 to 1.5 cm.

Anthers:

*Shape*.—Oblong.

*Length*.—Approximately 0.2 cm.

*Color*.—Near RHS Greyed-Yellowed 162B.

*Pollen*.—Not observed.

Pistil:

*Number*.—3.

*Length*.—Approximately 2.5 cm.

*Style*.—Length: Approximately 1.5 cm. Color: Near RHS White N155B.

Stigma:

*Shape*.—Linear, arching.

*Color*.—Near RHS White N155B.

*Ovary shape*.—Oblong.

*Ovary diameter*.—0.5 cm.

*Ovary length*.—1.0 cm.

*Ovary color*.—Near RHS Green 143C.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani*, Typical pests include; various species of *Thysanopthera*, various *Aphis* species, and various species of *Tetranychus*.

Temperature tolerance: USDA zones 3 through 10 tolerant.

What is claimed is:

1. A new and distinct cultivar of *Dianthus* plant named 'DCARE11-0' as herein illustrated and described.

* * * * *